United States Patent [19]

DeSatnick et al.

[11] Patent Number: 4,820,265
[45] Date of Patent: Apr. 11, 1989

[54] TUBING SET

[75] Inventors: Allen H. DeSatnick, Marblehead; Herbert D. Marcus, Winchester, both of Mass.; Kenneth E. Merte, Stillwater, Minn.

[73] Assignee: Minnesota Mining and Manufacturing Company, St. Paul, Minn.

[21] Appl. No.: 942,271

[22] Filed: Dec. 16, 1986

[51] Int. Cl.$^4$ ............................................. A61M 1/00
[52] U.S. Cl. ............................ 604/30; 128/748; 138/111; 604/34; 604/65; 604/118; 604/246; 604/284; 604/321
[58] Field of Search ............................ 604/22, 27–35, 604/43–45, 50, 51, 65–67, 118–121, 246–250, 257, 258, 280, 283, 284, 317, 318, 321; 128/748, 673, 675, 676; 137/594, 599; 138/111, 115, 118

[56] References Cited

U.S. PATENT DOCUMENTS

| Re. 31,873 | 4/1985 | Howes | 604/43 |
|---|---|---|---|
| 926,197 | 6/1909 | Kim | 604/185 |
| 2,478,876 | 8/1949 | Nelson | 604/31 |
| 2,697,435 | 12/1954 | Ray | 604/27 |
| 3,313,314 | 4/1967 | Burke et al. | 138/118 |
| 3,316,935 | 5/1967 | Kaiser et al. | 604/250 |
| 3,648,687 | 3/1972 | Ramsey, III | 128/673 |
| 3,912,168 | 10/1975 | Mullins et al. | 604/249 |
| 4,062,360 | 12/1977 | Bentley | 604/119 |
| 4,077,882 | 3/1978 | Gangemi | 128/748 |
| 4,226,124 | 10/1980 | Kersten | 604/118 |
| 4,273,070 | 6/1981 | Hoefelmayr | 138/111 |
| 4,314,480 | 2/1982 | Becker | 128/748 |
| 4,421,505 | 12/1983 | Schwartz | 604/28 |
| 4,604,089 | 8/1986 | Santangelo et al. | 604/5 |
| 4,648,406 | 3/1987 | Miller | 128/748 |
| 4,681,559 | 7/1987 | Hooven | 604/247 |

FOREIGN PATENT DOCUMENTS 0737249 6/1966 Canada ............................ 604/247
8600534 1/1886 PCT Int'l Appl. ................ 604/151

Primary Examiner—C. Fred Rosenbaum
Assistant Examiner—Mario Costantino
Attorney, Agent, or Firm—Donald M. Sell; Robert W. Hoke, II

[57] ABSTRACT

A tubing set, the major portions of which are defined from a trilumen section of tubing, comprises three lines including an inflow line, an outflow line and a pressure sensing line. The inflow line includes a header portion engageable about the rollers of a peristaltic pump, a delivery tube mounting a male luer fitting for engagement with a patient cannula, and a pair of clampable supply tubes with bag spikes for communication with saline bags. The pressure sensing line includes a pressure transmitting elongate tubular diaphragm mounted within a fluid chamber directly adjacent the patient end of the line. The pressure transmitting diaphragm communicates with an elongate dry or air tube which, at the remote end, communicates with an appropriate pump-mounted pressure transducer or the like. The outflow line includes a pressure control and relief assembly comprising a pair of parallel tubes respectively for association with a solenoid valve for the selective control of liquid flowing therethrough and for association with a mechanical relief valve for allowing flow therethrough and releasing pressure upon the occurrence of excess pressure. The outflow line also includes a terminal discharge tube incorporating a fluid trapping loop therein to preclude suction-defeating drainage of fluid upon deactivation of the system.

20 Claims, 2 Drawing Sheets

U.S. Patent    Apr. 11, 1989    Sheet 1 of 2    4,820,265
FIG. 1
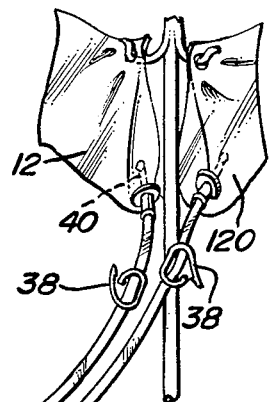
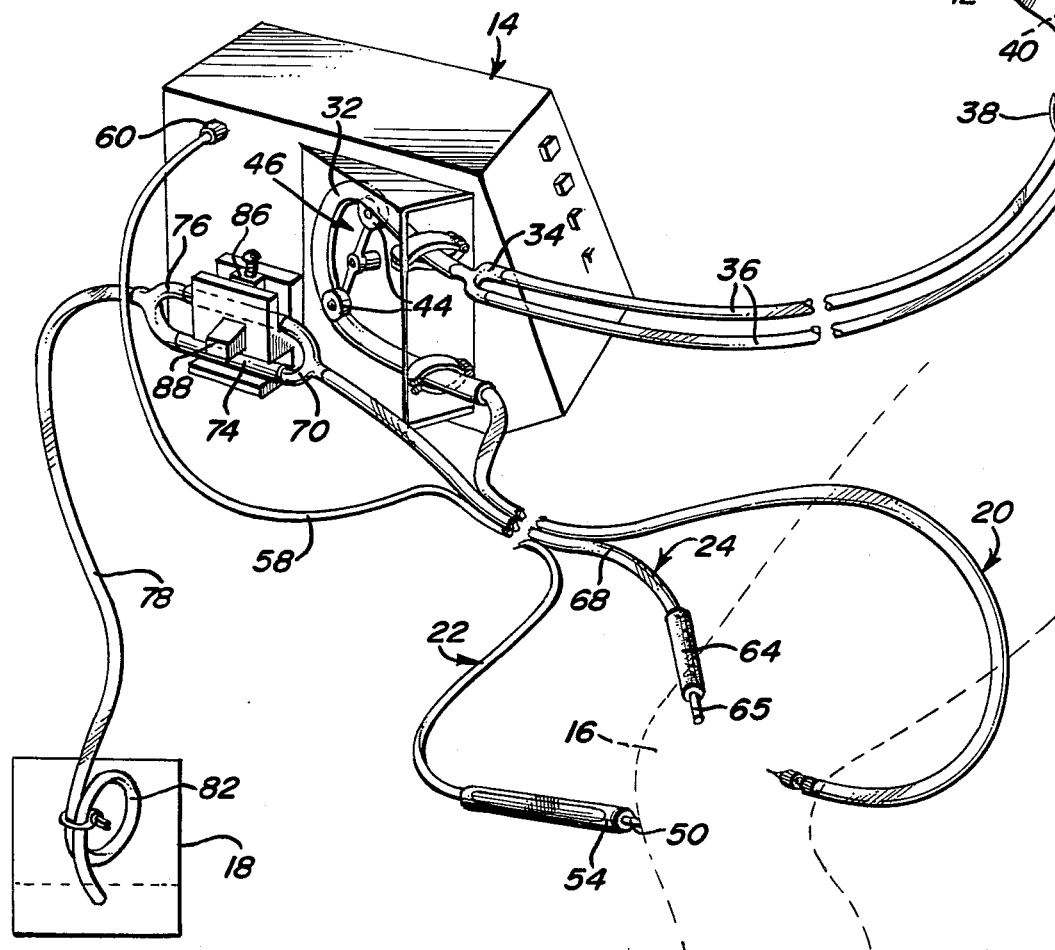
FIG. 5
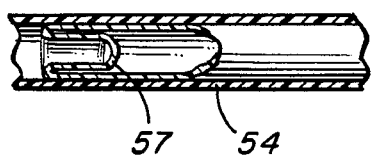
FIG. 7
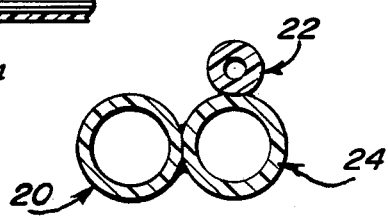
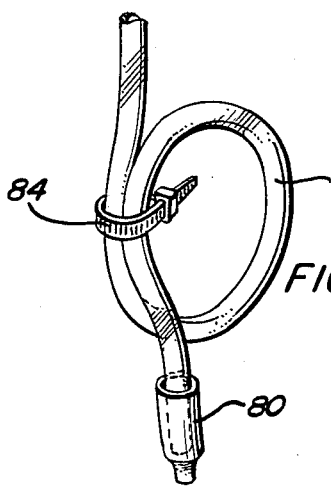
FIG. 6

TUBING SET

BACKGROUND OF THE INVENTION

The invention broadly relates to arthroscopic procedures and the control of irrigation and distention of the joint as normally required in such procedures. This control is preferably provided through maintainence of selected pressure and fluid flow rates within the joint. Inflation or distension is desirable for better visualization and access, while the flow of irrigation fluid, a function of the fluid flow rate, keeps the field of view clear and eliminates loose debris.

The need for independent control of the pressure and flow was recognized and addressed in copending application Ser. No. 760,171, filed July 29, 1985, and entitled "Irrigation System".

This "irrigation system" is schematically defined as including a positive displacement pump, preferably a peristaltic pump, and multiple conduits or tubing controlling flow to and from the pump, transmitting controlling pressure feedback, and the like.

Under preferred procedures, and in order to insure sterile conditions and eliminate cross-contamination between patients, replacement of all of the tubing prior to reuse of the equipment is essential. This can normally be quite complicated when multiple tubes are involved, and particularly so when the tubes themselves structurally vary from each other and, both in themselves and in conjunction with adjunct monitoring equipment, provide control functions.

SUMMARY OF THE INVENTION

The present invention is a tubing set, which is inserted as a unit, and is replaceable as such, in an arthroscopy pump system. The set preferably utilizes, as a significant aspect thereof, a trilumen construction. Provision of the tubing as a set insures proper replacement procedures wherein all of the tubing is supplied as a unit and assembled to the patient and pump system directly at the point of use of the pump system.

The tubing set, in addition to including basic inflow and outflow lines, specifically incorporates multiple control assemblies which, either in themselves or in cooperation with operating systems integral with or as adjunct to the arthroscopy pump, provide for the pressure and flow control essential to the effective functioning of the overall system. In connection therewith, the tubing set includes a pressure sensing line incorporating, at the patient end thereof, a pressure transmitting diaphragm, either a balloon diaphragm or a rolling diaphragm, which transfers liquid pressure from the surgery site to a column of air within the dry length of the remainder of the tube which communicates with an appropriate measurement transducer or the like at the pump.

The tubing set, as an integral part thereof, also incorporates a pressure control and relief assembly comprising dual parallel lines cooperating with a pump-associated solenoid control valve and a mechanical pressure relief valve. The pressure relief valve itself comprises a spring biased head controlled by a force equation which incorporates not only the internally generated pressure within the system, but also the resilient characteristics of the involved tubing itself.

Further, as the discharge of the overall irrigation system relies on a "suction" effect within the discharge line to "pull" fluid out of the knee, the tube set incorporates, as an integral component thereof, a liquid seal loop construction, referred to as "pigtail". This "pigtail" prevents system drainage, during periods of non-pressurization and through a trapping of fluid in the discharge line, to maintain the "suction" effect upon reactivation of the pressure.

The variously referred to subassemblies or means for controlling flow and pressure, while individually unique in the functioning thereof, are a part of the unitary tubing assembly, subjectable therewith to contamination during use and replaceable as a part thereof in readying the overall system for use.

These together with other features and advantages of the invention reside in the details of construction and manner of use of the tubing set as more fully hereinafter described.

DESCRIPTION OF THE DRAWINGS

FIG. 1 is a schematic perspective of an irrigation system incorporating the tubing set of the present invention;

FIG. 5 is a sectional detail similar to FIG. 4 illustrating another form of pressure diaphragm;

FIG. 6 is a perspective detail of the suction-maintaining pigtail on the discharge line; and FIG. 7 is a cross-sectional detail through the trilumen.

DESCRIPTION OF PREFERRED EMBODIMENT

Figure 2:
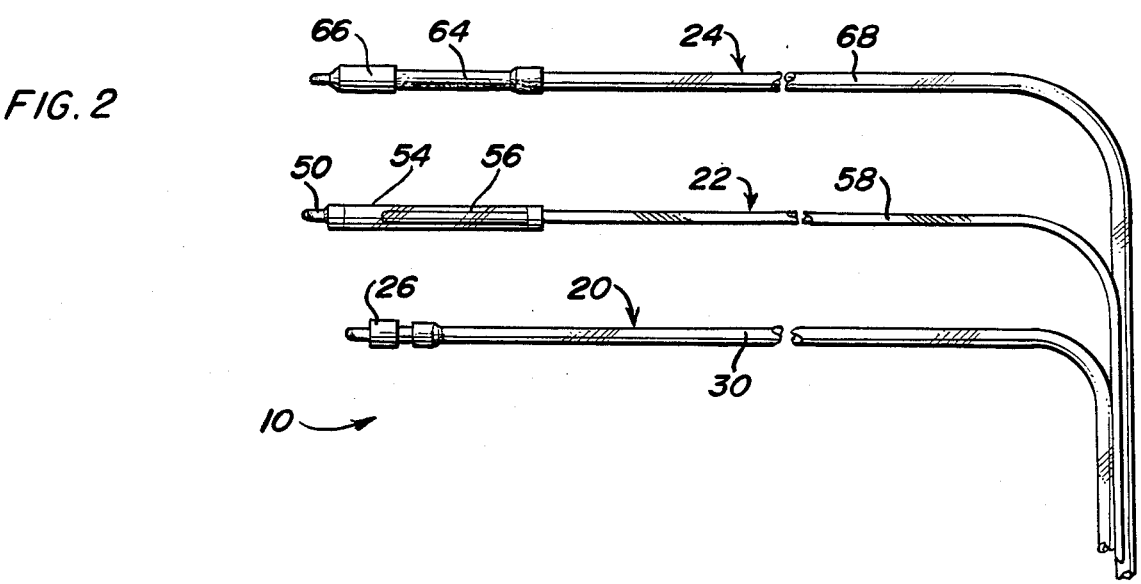
FIG. 2 is a plan view of the tubing set of the invention.
Figure 2:
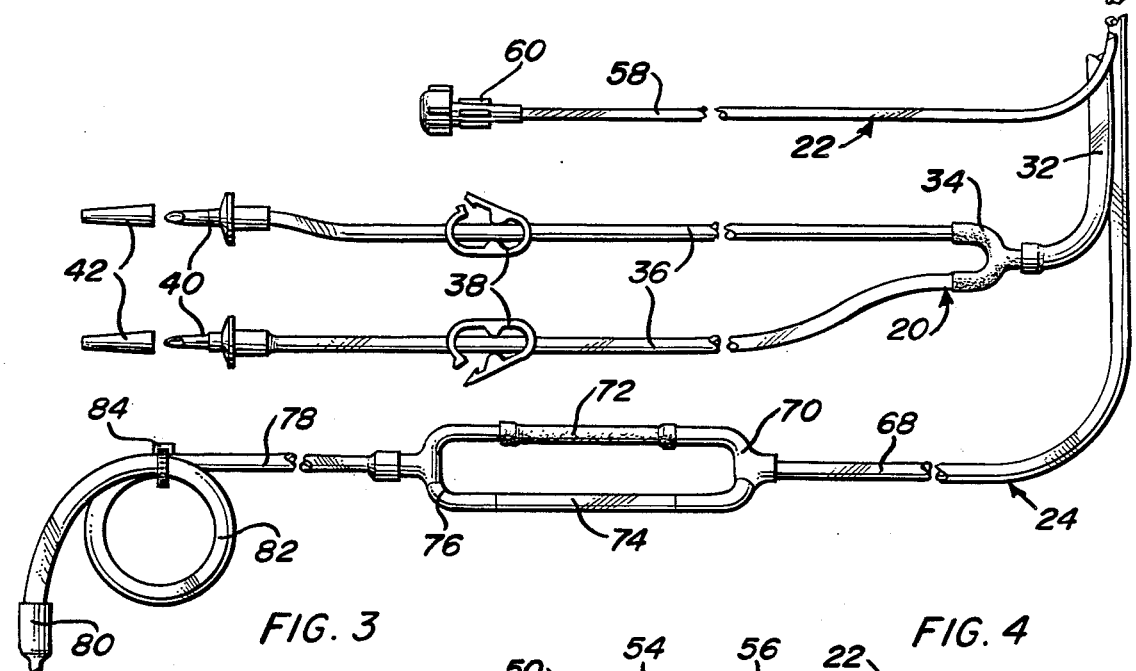

Referring now more specifically to the drawings, the arthroscopy tubing set 10 of the invention functions as a component of an irrigation system in arthroscopic procedures to channel flow of saline solution from hanging bags or bottles 12 through an arthroscopy pump 14 to the joint or site 16 of the procedure, at a flow rate and pressure set on the pump 14. Ultimately, the flow discharges to an appropriate collector 18. In order to facilitate handling of the tubing set, it is preferred that the tubing set be of a trilumen configuration with three parabonded PVC tubes separated at their ends to form three functionally different lines, an inflow line 20, a pressure sensing line 22 and and outflow line 24.

The inflow line 20 includes a capped male luer fitting 26 at the patient end.

The fitting 26 is bonded into a 133" long section of a delivery tube 30 having a 0.187" inside diameter and a 0.312" outside diameter. The tube 30 is in turn attached to a 13.5" PVC header tube 32 having a 0.375" inside diameter and a 0.5" outside diameter. The header tube connects to a "Y" connector 34 normally formed or cast from a plastisol. Two duplicate PVC supply tubes 36, approximately 46" long, extend from the "Y" connector. Each of these tubes has an inside diameter of 0.210" and an outside diameter of 0.312". A hand manipulable shut-off clamp 38 mounts on each tube 36 approximately 4" to 8" inward from the outer or terminal end thereof. The terminal end each of the tubes 36 is bonded to a separate bag spike 40 provided with a cap or protector 42 which is removed prior to a piercing engagement of the spike into one of the saline containers 12.

The header tube 32, engageable about the rollers 44 of the peristaltic unit 46 of the pump 14, is of a larger diameter than the delivery tube 30 as the diameter of the header tube is significant in developing the required flow. The diameter of the delivery tube 30 is desirably smaller for ease in handling, causing less problems in the field of operation.

It is also significant that the header tube be of a degree of rigidity within a specific durometer range to facilitate collapse of the tube so as to enable pumping action of the pump rollers 44. If durometer is too high, i.e., the tube is too rigid, the pump will not develop sufficient flow, and will necessarily work harder. If durometer is too soft, the life of the tubing will be reduced. Further, a too soft header tube 32 will also make it difficult to achieve sufficient flow as the tube will not expand to its full diameter when released by the rollers 44. A durometer of 68 has been found particularly satisfactory for a header tube as dimensioned above.

The pressure sensing line 22 includes a capped male luer pressure retaining fitting 50 bonded into one end of a 68 durometer, 3.75" PVC chamber 54 with a 0.312" inside diameter and a 0.438 outside diameter. The chamber 54 telescopically contains a resiliently collapsible 2.75" balloon diaphragm 56 of an approprite elastomer such as natural or synthetic latex or silicone rubber. The diaphragm 56 is a pressure transmitter and fluid barrier, and is bonded to and in fluid communication with a length of tube 58 projecting from the end of the chamber 54 remote from the luer fitting 50. This tube 58, which functions as a pressure tube to transmit sensed pressure, will normally be approximately 144" long with an internal diameter of 0.031" and an outside diameter of 0.135". The end of the pressure tube 58 remote from the chamber 54 has a capped female luer fitting 60 bonded thereto.

Alternatively, and as illustrated at 57 in FIG. 5, the pressure transmitting elastomer diaphragm can be in the nature of a rolling diaphragm which, upon being subjected to pressure at the leading end thereof within chamber 54, will inwardly roll within itself in a controlled manner.

In assembling the tubing set within an irrigation system, the male luer fitting 50 on the pressure sensing line 22 will be attached to a pressure sensing cannula (not shown). The female luer fitting 60 will in turn be attached to an appropriate male bulkhead fitting on the pump 14 where the actual pressure measurement is performed.

The pressure sensing line is basically dry, restricting liquid to the diaphragm-containing chamber 54 immediately adjacent the operating site.

For accurate pressure readings, it is essential that the pressure transmission medium be air rather than liquid. If liquid were used, any difference in height between the operating site and the measurement transducer at the pump, would reflect itself as an error in measurement. For example, a height difference of one foot would create an error of 22 mm. of mercury.

The use of air as the pressure transmission medium, as well as the design of the pressure sensing chamber 54 and line 58, minimizes any height error, and at the same time insures sterility at the operating site. The pressure tube 58 is kept as small as possible, since it is the compression of the volume of air in this tube, brought about by the collapsing of diaphragm 56 or inward rolling of diaphragm 57, that transmits the pressure. For example, assuming a chamber and tube relationship as shown, the introduction of only 1" of liquid into chamber 54 will result in a pressure change of 200 mm. of mercury in pressure line 58. Without chamber 54, it would require a displacement along the pressure tube 58 of approximately 30" of water, raising a possibility of introducing significant error, depending on the orientation of pressure line 58. Thus, the design of the pressure sensing line incorporating a short length of relatively large diameter tubing, as chamber 54, at the operating site, and a long length of very small diameter tubing 58, is highly desirable in providing accurate pressure readings.

The diaphragm 56 or 57 itself insures sterility at the operating site, isolating the operating site from the rest of the tubing 58 which connects to the non-sterile pump 14 and pressure transducer associated therewith. The diaphragm 56 or 57 also prevents introduction of any liquid into the small diameter pressure tube 58. As will be noted in the drawings, the balloon diaphragm 56 and the rolling diaphragm are each generally in the nature of an elongate closed tubular member extending centrally along substantially the entire length of the tubular chamber 54. The relationship of diaphragm size to chamber size must be such as to maintain sensitivity within desired parameters. Further, the contained volume of the diaphragm must be sufficient to transmit the maximum required pressure when fully compressed or rolled. By the same token, the material and thickness of the diaphragm must not introduce any significant pressure drop or error in the measurement.

The outflow line 24 includes a tubular elastomeric adapter 64 of natural or synthetic latex or silicone rubber at the patient end. This adapter 64 is approximately 4" long and includes a 0.187" inside diameter with a 0.312" outside diameter. The outer or free end of the adapter is provided with a protective cap 66 of a distinctive color, preferably blue, providing an easily distinguished visual indication of the patient end of the tubing set.

The elastomer adapter 64 is bonded to a tube 68 approximately 136" long with an inside diameter of 0.187" and an outside diameter of 0.312". The tube 68 is in turn bonded to a plastisol "Y" 70, the two branches of which are bonded to a pair of parallel tubes approximately 3.5" long. The first tube 72 is an elastomer tube, for example of latex or silicone rubber, with an inside diameter of 0.250" and a wall thickness of 1/32". The second tube 74 is PVC tubing with a durometer of 39. This second tube 74 has an inside diameter of 0.250" and an outside diameter of 0.312". The two parallel tubes 72 and 74 are rejoined by a second plastisol "Y" connector 76 which in turn is bonded to and in communication with a discharge tube 78 approximately 48" long. The tube 78 has an inside diameter of 0.210" and an outside diameter of 0.312". The free remote end of the tube 78 is provided with a distinctively colored cap 80, preferably red and easily distinguished from the opposed end cap 66, again to provide a ready and immediate identification of each end of the tubing set. Approximately 4" from the capped end of the tube 78, the discharge tube 78 is provided with one complete coil 82 defining a "pigtail" configuration forming a liquid seal. An appropriate cable tie or the like 84 is wrapped around the coil to retain the configuration thereof.

In use, the outflow line 24 will be attached to the outflow port or drainage cannula 65, at the operating site, by the tubular latex or silicone rubber adapter 64.

The parallel branches or tubes 72 and 74, in the outflow line, constitute a portion of the pressure control and relief assembly and are respectively engaged with a mechanical pressure relief valve 86 and a solenoid control valve 88. Finally, the looped free end of the outflow line, which facilitates the siphoning effect required in the irrigation system described in the copending application, is placed within a bucket or other drainage container 18 to receive the spent flow.

With specific reference to the pressure control and relief assembly, comprising the parallel elastomer and PVC tubes 72 and 74 and the "Y" adapters 70 and 76, both the configuration and dimensions thereof are considered significant in fitting the assembly to the control valve units and routing the tubes 72 and 74 through both the mechanical relief valve 86 and the solenoid control valve 88 without crimping. As noted in FIG. 1, both the mechanical pressure relief valve 86 and the solenoid control valve 88 can be provided as components on the overall pump assembly 14. It will also be noted that, as illustrated in FIGS. 1, 2 and 3, the flow in the pressure control and relief assembly is from right to left.

The PVC tube 74, constituting the solenoid control valve tube, is routed through the solenoid valve 88 for cooperation therewith in providing control of the outflow in response to sensed pressure. The specific operation of the solenoid valve and the interrelationship between this operation and the sensed pressure is broadly referred to in the copending application. The wall thickness, inside diameter and durometer of the solenoid control valve tube 74, as related to the associated solenoid valve, is significant in insuring proper control of flow and proper action of the solenoid, particularly as it is contemplated the tube itself will supply the restoring force for opening the solenoid. Basically, if the inside diameter is too small, or the wall thickness too great, maximum flow capabilities will be diminished. Further, if the wall thickness is too small or the inside diameter too large, an action of the solenoid will not be correct since the restoring force provided by the inherent memory or resiliency of the tube will not be sufficient.

With reference to the latex or silicone rubber tube 72, comprising a pressure relief valve tube, the design of this tube is closely associated with the design of the mechanical pressure relief valve 86 itself.

Figure 3:
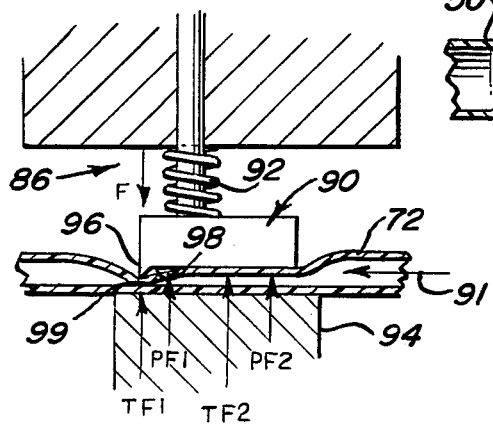
FIG. 3 is an enlarged sectional detail through the pressure relief component of the tubing set in cooperative operable position within a mechanical pressure release valve.
Figure 4:
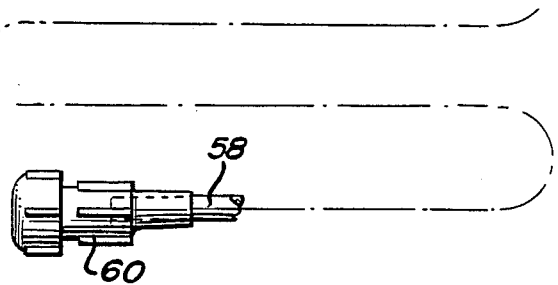
FIG. 4 is a detailed illustration of the pressure sensor diaphragm component and the associated pressure sensing line.

Noting the detail view of FIG. 3, the pressure relief valve 86 includes a reciprocating head 90 elongate relative to the length of the received pressure relief tube 72. The direction of flow in the pressure control and relief assembly, and in particular in tube 72 is indicated by arrow 91. The head 90 is spring loaded, by appropriate spring means 92, to engage and pinch off the pressure relief tube against a rigid base 94. The pinch closing of the tube 72 is in conjunction with a partial constriction of the tube 72 upstream of the pinch area and for the length of the head 90 upstream of the pinch area. The actual pinch closing of tube 72 is effected by a depending pinch edge portion 96 which projects relative to the tube engaging underface 98 of the head a sufficient distance to provide, as illustrated in FIG. 3, the pinch closing of the tube 72 in conjunction with the desired partial constriction of the tube upstream of the pinch area.

From an analysis of the forces involved, it will be noted that the total closing force F is opposed by the resistance of the tubing itself at the pinch tip 96 (TF1), the resistance of the tubing along the extended length of the hammer (TF2), the force applied to the pinch point as a result of the liquid pressure in the tubing (PF1), and the force applied to the extended length of the hammer as a result of the liquid pressure (PF2). As the liquid pressure in the pressure relief valve tube 72 increases, both PF1 and PF2 will increase until the sum total of TF1 plus TF2 plus PF1 plus PF2 equal F. At this point, the mechanical valve will be in equilibrium and any further increase in the pressure will cause the hammer 90 to move up against the force of spring 92, compressing spring 92 and allowing flow through the valve 86 with a resultant reduction of pressure regardless of the position of the solenoid valve on parallel line 74. The spring 92 is to be designed to have a nearly constant force regardless of its displacement within the operating limits, the valve allowing increase of pressure up to its set point, and then opening so the pressure cannot exceed the set point by any significant amount. It will be appreciated that the characteristics of the tube 72 itself play an important part in the proper operation of the valve. Thus, it will be necessary to carefully select the properties of the tubing used in the valve 86, and in particular its diameter, durometer and wall thickness, all of which will be related to the specific operational parameters of the valve 86. It is also to be appreciated that there must be little or substantially no tendency for the tubing to stick to itself.

The loop or "pigtail" configuration 82, in the discharge tube 78 of the discharge line 24 downstream of the pressure control and relief assembly, is significant in ensuring proper operation of the system. Basically, the "pigtail" 82 provides a liquid seal which maintains a column of liquid in the discharge tube extending from the loop 82 to the solenoid valve 88. Without the "pigtail" 82, when the pressure control solenoid 88 closes, the fluid in the discharge tube 78 will drain into the collector or receptacle 18, and air will be introduced into the line. This will result in inaccuracies and delays in reestablishing flow and pressure within desired parameters. Proper operation of the system requires the "suction" effect of the liquid flow in the discharge line to "pull" fluid out of the knee or joint when the solenoid valve is open. If the liquid in the discharge tube is allowed to drain during intermittent closing of solenoid valve 88, when solenoid valve 88 opens, the siphon will be momentarily absent and there will be only positive pressure in the knee to "push" fluid through the discharge. This results in erratic operation of the dynamics of the system, with varying pressures and flows. The "pigtail" 82, acting in the manner of a liquid trap or seal, prevents drainage of the line when the solenoid is closed and thus, in a unique manner, solves a particularly vexing problem and provides in effect for a "continuous" intermittent siphon operation.

While not specifically described, it will be appreciated that the joining of the various tubes in the formation of the individual lines is to be effected in a manner providing for sealed communication between the tubes. This may entail a direct bonding of the tubes to each other, possibly through a telescopic interfit, or the use of adapters.

Further, while the tube specifications have been set forth with substantial specificity, and while significant aspects of the invention are attributable thereto, minor tolerances are contemplated. While the majority of the components or tubes of tubing set are of PVC with appropriate wall thicknesses capable of accommodating the internal pressures of the system, the pressure relief valve tube 72 is specifically formed of an elastomer for the enhanced flexibility thereof desired for proper operation of the mechanical pressure relief valve. Similarly, a length of relatively thick walled latex or silicone rubber 64 is provided at the patient end of the outflow line to facilitate an expansion of this line end portion and frictional engagement with an outlet port at the operation site.

In installing the tubing set prior to commencing the arthroscopic procedure, the pump is initially put in the off position and saline bags hung just above the level of the pump. Using sterile techniques, the tubing set is delivered to the scrub nurse. The scrub nurse, in turn, will pass the red-capped equipment end of the tubing set to the circulating nurse. The scrub nurse will then secure the excess tubing and the blue-capped patient-end of the tubing to the sterile field on the draped patient. The circulating nurse will close the clamps 38 on the inflow line 20. The inflow line will then be connected to the pump by engaging the header tube 32 around the pump rollers 44. To facilitate this installation, flow direction indicating arrows can be provided on the pump. The bag spikes will be connected to the saline bags 12.

The pressure sensing or monitoring line 22 will be connected to the appropriate port on the pump and subsequently connected to the patient cannula.

With regard to the outflow line 24, and in particular the pressure control and relief assembly comprising the parallel lines 72 and 74, the relatively stiffer PVC control tube 74 is mounted in operative position within the solenoid valve assembly 88. The relatively more flexible elastomer pressure relief tube 72 is in turn inserted in operative position within the mechanical relief valve unit 86. Directional arrows may be provided in conjunction with the valve units to insure proper directional positioning of the tubes 72 and 74. Finally, the looped or "pigtail" end portion of the outlet flow line tube 78 is placed within an appropriate collector or liquid collecting receptacle 18 open to the ambient air. The irrigation system, with a new sterile tubing set installed, is now ready for use.

We claim:

1. For use in an arthroscopic irrigation system, a replaceable unitary tubing set, said set including three distinct elongate fluid lines joined, for a substantial portion of the central length of each, in parallel non-communicating relationship, said lines comprising an inflow line, an outflow line, and a pressure sensing line, said lines having first laterally separated end lengths extending from one end of the joined central lengths and terminating in patient communicating outer ends, said lines having second laterally separated end lengths extending from the other end of the joined central lengths and including equipment engaging components therealong, and wherein the first separated end length of said inflow line comprises a pair of inflow supply tubes each terminating in an outer end including means for communication with a source of liquid, a single header tube between and in liquid passing communication with said pair of supply tubes and the central length of the inflow line, and means on said supply tubes for selectively closing and opening these tubes relative to flow therethrough.

2. For use in an arthroscopic irrigation system, a replaceable unitary tubing set, said set including three distinct elongate fluid lines joined, for a substantial portion of the central length of each, in parallel non-communicating relationship, said lines comprising an inflow line, an outflow line, and a pressure sensing line, said lines having first laterally separated end lengths extending from one end of the joined central lengths and terminating in patient communicating outer ends, said lines having second laterally separated end lengths extending from the other end of the joined central lengths and including equipment engaging components therealong, and wherein the first separated end length of said inflow line comprises a pair of inflow supply tubes each terminating in an outer end including means for communication with a source of liquid, a single header tube between and in liquid passing communication with said pair of supply tubes and the central length of the inflow line, and means on said supply tubes for selectively closing and opening these tubes relative to flow therethrough, and wherein the second separated end length of said inflow line comprises a delivery tube, said delivery tube and central length of the inflow line being of a substantially constant internal diameter, said header tube defining a pumping component for pumping liquid from the source to said delivery tube, said header tube having an internal diameter greater than the constant internal diameter of said delivery tube.

3. The tubing set of claim 2 wherein the first separated end length of said outflow line further includes a pressure control and relief assembly inward of said discharge tube, said assembly comprising a pair of laterally spaced elongated flow regulating tubes forming a pair of parallel flow passages, each communicating, at one end thereof, with said discharge tube and, at the second end thereof, with the central length of the outflow line, one of said pair of flow regulating tubes defining a flow control tube operably cooperable with a control valve for a controlled varying of the flow passage therethrough and a corresponding control of the flow through said flow passage to maintain the pressure within the irrigation system within normal pressure parameters, the second of said pair of flow regulating tubes defining a pressure relief tube operably cooperable with a pressure relief valve for closing the flow passage therethrough within normal pressure parameters in the flow control tube, the flow passage through said pressure relief tube being selectively openable in response to internal pressures above normal pressure parameters.

4. The tubing set of claim 3 wherein said flow control tube, relative to said pressure relief tube, has a substantially greater resistance to flow passage distortion in response to internal/external pressure differentials.

5. The tubing set of claim 4 wherein said flow control tube is a PVC tube with a wall thickness of approximately 1/16", and said pressure relief tube is an elastomeric tube with a wall thickness of approximately 1/32".

6. The tubing set of claim 5 wherein the first separated end length of said pressure sensing line includes a free end with a patient-communicating fitting thereon, an elongate tubular pressure chamber in said pressure sensing line immediately inward of said fitting, said chamber having a first end communicating with said fitting and a second end communicating with the remainder of the pressure sensing line, a pressure transmitting resiliently flexible diaphragm within said chamber, said diaphragm defining a fluid seal therein precluding passage of patient-originating liquid through the second end of said chamber, said remainder of the pressure sensing line defining a column of pressure transmitting air responsive to but segregated from the patient originating liquid.

7. The tubing set of claim 6 wherein said diaphragm comprises an elongate generally tubular configuration received centrally along said chamber, said diaphragm having a sealed first end directed toward the first end of said chamber, said diaphragm having an open second end sealed to the chamber peripherally about the second end of the chamber and opening into the remainder of the pressure sensing line whereby a liquid-pressure-induced contraction of the tubularly configured diaphragm will pressurize air within the remainder of the pressure sensing line for sensing at the end thereof remote from the pressure chamber.

8. The tubing set of claim 7 wherein the joined central lengths are selectively severable from each other along selected portions thereof.

9. For use in an arthroscopic irrigation system, a replaceable unitary tubing set, said set including three distinct elongate fluid lines joined, for a substantial portion of the central length of each, in parallel noncommunicating relationship, said lines comprising an inflow line, an outflow line, and a pressure sensing line, said lines having first laterally separated end lengths extending from one end of the joined central lengths and terminating in patient communicating outer ends, said lines having second laterally separated end lengths extending from the other end of the joined central lengths and including equipment engaging components therealong, and wherein the first separated end length of said inflow line comprises a pair of inflow supply tubes each terminating in an outer end including means for communication with a source of liquid, a single header tube between and in liquid passing communication with said pair of supply tubes and the central length of the inflow line, and means on said supply tubes for selectively closing and opening these tubes relative to flow therethrough, and wherein the second separated end length of said inflow line comprises a delivery tube, said delivery tube and central length of the inflow line being of a substantially constant internal diameter, said header tube defining a pumping component for pumping liquid from the source to said delivery tube, said header tube having an internal diameter greater than the constant internal diameter of said delivery tube, and wherein the first separated end length of said outflow line includes a discharge tube terminating in an outer discharge end, said discharge tube, inward of said discharge end, including liquid seal means for selective trapping of a liquid column within said discharge tube.

10. For use in an arthroscopic irrigation system, a replaceable unitary tubing set, said set including three distinct elongate fluid lines joined, for a substantial portion of the central length of each, in parallel noncommunicating relationship, said lines comprising an inflow line, an outflow line, and a pressure sensing line, said lines having first laterally separated end lengths extending from one end of the joined central lengths and terminating in patient communicating outer ends, said lines having second laterally separated end lengths extending from the other end of the joined central lengths and including equipment engaging components therealong, and wherein the first separated end length of said inflow line comprises a pair of inflow supply tubes each terminating in an outer end including means for communication with a source of liquid, a single header tube between and in liquid passing communication with said pair of supply tubes and the central length of the inflow line, and means on said supply tubes for selectively closing and opening these tubes relative to flow therethrough, and wherein the second separated end length of said inflow line comprises a delivery tube, said delivery tube and central length of the inflow line being of a substantially constant internal diameter, said header tube defining a pumping component for pumping liquid from the source to said delivery tube, said header tube having an internal diameter greater than the constant internal diameter of said delivery tube, and wherein the first separated end length of said outflow line includes a discharge tube terminating in an outer discharge end, said discharge tube, inward of said discharge end, including liquid seal means for selective trapping of a liquid column within said discharge tube, and wherein said liquid seal means is a closed loop defined by a 360° turn in said discharge tube.

11. For use in an arthroscopic irrigation system, a replaceable unitary tubing set, said set including three distinct elongate fluid lines joined, for a substantial portion of the central length of each, in parallel noncommunicating relationship, said lines comprising an inflow line, an outflow line, and a pressure sensing line, said lines having first laterally separated end lengths extending from one end of the joined central lengths and terminating in patient communicating outer ends, said lines having second laterally separated end lengths extending from the other end of the joined central lengths and including equipment engaging components therealong, and wherein the first separated end length of said outflow line includes a discharge tube terminating in an outer discharge end, said discharge tube, inward of said discharge end, including liquid seal means for selective trapping of a liquid column within said discharge tube constituting a closed loop defined by, a 360° turn in said discharge tube.

12. The tubing set of claim 11 wherein the first separated end length of said outflow line further includes a pressure control and relief assembly inward of said discharge tube, said assembly comprising a pair of laterally spaced elongated flow regulating tubes forming a pair of parallel flow passages, each communicating, at one end thereof, with said discharge tube and, at the second end thereof, with the central length of the outflow line, one of said pair of flow regulating tubes defining a flow control tube operably cooperable with an external control valve mechanism for a controlled varying of the flow passage therethrough and a corresponding control of the flow through said flow passage to maintain the pressure within the irrigation system within normal pressure parameters, the second of said pair of flow regulating tubes defining a pressure relief tube operably cooperable with an external pressure relief valve mechanism for closing the flow passage therethrough within normal pressure parameters in the flow control tube, the flow passage through said pressure relief tube being selectively openable in response to internal pressures above normal pressure parameters.

13. The tubing set of claim 12 wherein said flow control tube, relative to said pressure relief tube, has a substantially greater resistance to flow passage distortion in response to internal/external pressure differentials.

14. For use in an arthroscopic irrigation system, a replaceable unitary tubing set, said set including three distinct elongate fluid lines joined, for a substantial portion of the central length of each, in parallel noncommunicating relationship, said lines comprising an inflow line, an outflow line, and a pressure sensing line, said lines having first laterally separated end lengths extending from one end of the joined central lengths and terminating in patient communicating outer ends, said lines having second laterally separated end lengths extending from the other end of the joined central lengths and including equipment engaging components therealong, and wherein the first separated end length of said pressure sensing line includes a free end with a patient-communicating fitting thereon, an elongate tubular pressure chamber in said pressure sensing line immediately inward of said fitting, said chamber having a first end communicating with said fitting and a second end communicating with the remainder of the pressure sensing line, a pressure transmitting rsiliently flexible diaphragm within said chamber, said diaphragm defining a fluid seal therein precluding passage of patient-originating liquid through the second end of said chamber, said remainder of the pressure sensing line defining a column of pressure transmitting air responsive to but segregated from the patient originating liquid.

15. The tubing set of claim 14 wherein said diaphragm comprises an elongate generally tubular configuration received centrally along said chamber, said diaphragm having a sealed first end directed toward the first end of said chamber, said diaphragm having an open second end sealed to the chamber peripherally about the second end of the chamber and opening into the remainder of the pressure sensing line whereby a liquid-pressure-induced collapsing of the tubularly configured diaphragm will pressurize air within the remainder of the pressure sensing line for sensing at the end thereof remote from the pressure chamber.

16. In a tubing set for a surgical irrigation system, an outflow line for fluid discharge from an operation site, said outflow line comprising a flow tube, a discharge tube and a pressure control and relief assembly interposed between and joining the flow tube and the discharge tube, said pressure control and relief assembly comprising a pair of laterally positioned elongate tubes forming a pair of parallel flow passages, each communicating, at the opposite ends thereof, with said flow tube and said discharge tube, said pair of tubes defining a flow control tube and a pressure relief tube, said flow control tube being operably cooperable with a control valve for a controlled varying of the flow passage therethrough and a corresponding control of the fluid discharge therethrough to maintain the resultant pressure within the irrigation system within normal pressure parameters, said pressure relief tube being operably cooperable with a pressure valve for a closing of the flow passage therethrough within normal pressure parameters in the flow control tube, the flow passage through said pressure relief tube being selectively openable in response to internal pressures above normal pressure parameters, and wherein said flow control tube, relative to said pressure relief tube, has a substantially different resistance to flow passage distortion in response to internal/external pressure differentials applied in a pump and valve system.

17. In the tubing set of claim 16, said discharge tube terminating in an outer discharge end, said discharge tube, inward of said discharge end, including liquid seal means for selective trapping of a liquid column within said discharge tube.

18. In the tubing set of claim 17 wherein said liquid seal means is a closed loop defined by a 360° turn in said discharge tube.

19. In a tubing set for a surgical irrigation system, an outflow line for fluid discharge from an operation site, said outflow line comprising a flow tube, a discharge tube and a pressure control and relief assembly interposed between the flow tube and the discharge tube for controlling the flow discharge through said outflow line, said discharge tube terminating in an outer discharge end, said discharge tube, inward of said discharge end, including a liquid seal means for selective trapping of a liquid column within said discharge tube and for maintaining a static head above said seal whereby when the supply to said outflow line is interrupted, a static head is maintained in said outflow line above said seal.

20. In the tubing set of claim 19 wherein said liquid seal means is a closed loop defined by a 360° turn in said discharge tube.

* * * * *